United States Patent
Maloney et al.

(10) Patent No.: US 10,342,752 B2
(45) Date of Patent: Jul. 9, 2019

(54) TOOTH WHITENING ORAL CARE PRODUCT

(71) Applicant: COLGATE-PALMOLIVE COMPANY, New York, NY (US)

(72) Inventors: Venda P. Maloney, Piscataway, NJ (US); Suman K. Chopra, Monroe, NJ (US); Rahul Patel, Parsippany, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/107,569

(22) PCT Filed: Dec. 23, 2013

(86) PCT No.: PCT/US2013/077373
§ 371 (c)(1),
(2) Date: Jun. 23, 2016

(87) PCT Pub. No.: WO2015/099638
PCT Pub. Date: Jul. 2, 2015

(65) Prior Publication Data
US 2016/0331663 A1  Nov. 17, 2016

(51) Int. Cl.
| | | |
|---|---|---|
| *A61Q 11/00* | (2006.01) |
| *A61K 8/11* | (2006.01) |
| *A61K 9/70* | (2006.01) |
| *A61K 31/717* | (2006.01) |
| *A61K 8/73* | (2006.01) |
| *A61K 8/49* | (2006.01) |
| *A61K 8/02* | (2006.01) |
| *A61K 8/25* | (2006.01) |
| *A61K 8/34* | (2006.01) |
| *A61K 8/46* | (2006.01) |
| *A61K 8/58* | (2006.01) |
| *A61K 8/60* | (2006.01) |
| *A61K 8/81* | (2006.01) |

(52) U.S. Cl.
CPC ............ *A61K 8/731* (2013.01); *A61K 8/0216* (2013.01); *A61K 8/0254* (2013.01); *A61K 8/25* (2013.01); *A61K 8/345* (2013.01); *A61K 8/463* (2013.01); *A61K 8/492* (2013.01); *A61K 8/58* (2013.01); *A61K 8/60* (2013.01); *A61K 8/8111* (2013.01); *A61K 8/8141* (2013.01); *A61K 8/8164* (2013.01); *A61Q 11/00* (2013.01); *A61K 2800/30* (2013.01); *A61K 2800/41* (2013.01); *A61K 2800/43* (2013.01); *A61K 2800/48* (2013.01); *A61K 2800/5424* (2013.01); *A61K 2800/594* (2013.01); *A61K 2800/596* (2013.01); *A61K 2800/5922* (2013.01)

(58) Field of Classification Search
CPC ...... A61Q 11/00; A61K 8/731; A61K 8/0283; A61K 8/11; A61K 2800/43; A61K 2800/56
See application file for complete search history.

(56) References Cited

U.S. PATENT DOCUMENTS

| | | | |
|---|---|---|---|
| 3,535,421 A | 10/1970 | Briner et al. | |
| 3,538,230 A | 11/1970 | Pader et al. | |
| 3,678,154 A | 7/1972 | Widder et al. | |
| 3,862,307 A | 1/1975 | DiGiulio | |
| 3,937,807 A | 2/1976 | Haefele | |
| 3,959,458 A | 5/1976 | Agricola et al. | |
| 4,051,234 A | 9/1977 | Gieske et al. | |
| 4,340,583 A | 7/1982 | Wason | |
| 4,842,847 A | 6/1989 | Amjad | |
| 4,866,161 A | 9/1989 | Sikes et al. | |
| 4,885,155 A | 12/1989 | Parran, Jr. et al. | |
| 5,004,597 A | 4/1991 | Majeti et al. | |
| 5,292,526 A | 3/1994 | Gaffar et al. | |
| 6,419,903 B1 * | 7/2002 | Xu | A61K 8/0208 424/401 |
| 8,647,648 B2 | 2/2014 | Boyd et al. | |
| 9,744,112 B2 | 8/2017 | Szewczyk et al. | |
| 2003/0095931 A1 | 5/2003 | Stier | |
| 2007/0122455 A1 | 5/2007 | Myers et al. | |
| 2007/0148213 A1 * | 6/2007 | Ibrahim | A61K 8/0208 424/443 |
| 2008/0152599 A1 | 6/2008 | Brignoli et al. | |
| 2010/0173003 A1 | 7/2010 | Sengupta et al. | |
| 2013/0095159 A1 | 4/2013 | Boyd et al. | |

FOREIGN PATENT DOCUMENTS

| | | | |
|---|---|---|---|
| EP | 1891937 | 2/2008 | |
| EP | 1935395 | 6/2008 | |
| WO | WO201212341 | 9/2002 | |
| WO | WO03015748 | 2/2003 | |
| WO | WO2009006218 | 1/2009 | |
| WO | WO 2012002946 A1 * | 1/2012 | ............... A61K 8/02 |
| WO | WO 2012087328 A1 * | 6/2012 | ............... A61K 8/02 |
| WO | 2012/123241 | 9/2012 | |
| WO | WO201308759 | 6/2013 | |
| WO | WO2013089760 | 6/2013 | |

OTHER PUBLICATIONS

Corresponding International Search Report and Written Opinion for PCT/US2013/077377 dated Apr. 15, 2014.
Joiner, "A novel optical approach to achieving tooth whitening." J Dent. (2008);36 S8-14.
"A Review of the Principle Advantages of METHOCEL in Tablet Coatings", the DOW Company, Jul. 2002, pp. 1-31.
Joiner, 2010, "Whitening toothpastes: A review of the literature," Journal of Dentistry 385:e17-e24.

* cited by examiner

Primary Examiner — Tracy Liu

(57) ABSTRACT

A tooth whitening composition containing film flakes of a hydroxyalkyl methyl cellulose and a pigment in combination with an orally acceptable carrier vehicle.

19 Claims, No Drawings

TOOTH WHITENING ORAL CARE PRODUCT

CROSS-REFERENCE TO RELATED PATENT APPLICATIONS

The present application is a U.S. national stage application under 35 U.S.C. § 371 of PCT Application No. PCT/US2013/077373, filed Dec. 23, 2013, the entirety of which is incorporated herein by reference.

BACKGROUND

Many individuals are dissatisfied with their current tooth color. Thus, there is a desire for whiter teeth and one means to achieve whiter teeth is the use of tooth whitening products.

It is known in the literature that the visual perception of a white substance can be altered through the deposition of an optical brightener, blue pigment or blue dye, especially one for which the hue angle (in the CIELAB scale) of the reflected or emitted light is between 200 to 320 degrees. This effect is commonly used in laundry detergent products to make white clothes appear "whiter" to the human eye. The same concept has been applied to tooth whitening as well. The natural off-white or yellow color of teeth can be made to appear whiter through the deposition of a blue substance onto teeth. Using pigments with a deposition aid, i.e., high molecular weight Gantrez®, type polymers (copolymers of maleic anhydride and with methyl vinylether) in toothpaste to make teeth look whiter is disclosed in EP 1935395B1.

It would be desirable to have tooth whitening oral care products containing pigments and polymers other than Gantrez® that can produce superior temporary tooth whitening effects when incorporated into oral care products.

BRIEF SUMMARY

A tooth whitening oral care composition comprising:
(i) flakes of a water soluble whitening film comprising (a) a film forming polymer comprising hydroxyalkyl cellulose wherein the hydroxyalkyl cellulose has a viscosity of about 1 to less than about 1000 millipascal seconds (mPa·s) as determined as a 2% by weight aqueous solution of the polymer at 20° C. using a Ubbelohde tube viscometer; and (b) a pigment having a blue to blue-violet color with a hue angle in the CIELAB system ranging from 200 to 320 degrees,
wherein the film is preferably free of starch and wherein the flakes have a dissolution rate of about 30 seconds or less, and
(ii) an orally acceptable carrier vehicle.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

The term "free of starch" means that no starch is added to the film forming ingredients and the resulting film contains no measurable amount of starch.

The film forming polymer comprises a hydroxyalkyl cellulose polymer. In one embodiment the film forming polymer consists essentially of a hydroxyalkyl cellulose polymer, that is, no other film forming polymers, such as starch or Gantrez® is present in the film.

In accordance with the present invention there is provided an oral composition, e.g., a dentifrice, having suspended therein flakes of a water soluble film (sometimes referred to herein as "film flakes") comprised of a mixture, typically homogeneous, of a water soluble hydroxyalkyl cellulose polymer, the film matrix having entrained therein a pigment having a blue to violet color with a hue angle in the CIELAB system ranging from 200 to 320 degrees.

In preparing film flakes according to the present invention the hydroxyalkyl cellulose and pigment, are dissolved in a compatible solvent (e.g., water, ethyl acetate, acetone, an alcohol such as ethanol, or mixtures thereof) to form a film forming composition. Optionally, other ingredients may be added, e.g., a flavorant, humectant (e.g., propylene glycol), surfactant (e.g., Tween 80), sweetener, active agent and the like. The optional ingredients can be present in the film, in the non-film portion of the oral composition or both, more detailed descriptions of such optional ingredients are provided hereinafter. The film forming composition is cast on a releasable carrier and dried to form a sheet of film matrix material. The carrier material must have a surface tension which allows the film solution to spread evenly across the intended carrier width without soaking to form a destructive bond between the film carrier substrates. Examples of suitable carrier materials include glass, stainless steel, Teflon and polyethylene-impregnated paper. Drying of the film may be carried out at high temperature using a drying oven, drying terminal, vacuum drier, or any other suitable drying equipment which does not adversely affect the ingredients of which the film is composed.

The film thickness ranges in size from about 1-5 mil, or about 1-4 mil or about 1.5-5 mil or about 1.5-3 mil, or about 2-3 mil or about 2 mil.

Once the film is formed, the film flakes are made from the film, for example by punching or cutting the film into various shaped flakes such as hearts, squares, rectangles, triangles, stars, diamonds, circles, and the like. Optionally, the film may be ground in to irregular shapes using convention grinding techniques known in the art. The particle size of the film flakes typically are such that greater than 90% of the particles pass through a 50 mesh filter. In some embodiments the particle size is between 30 to 100 mesh, or 30 to 80 mesh, or 50 to 80 mesh. The film flakes are incorporated in the oral composition of the present invention at a concentration of about 0.05 to 5.0% by weight, in one embodiment about 0.05 to 2%, in another embodiment about 0.05 to 1%, and in another embodiment about 0.1 to about 0.5% by weight.

The film flakes of the invention have a rapid dissolution rate, e.g., about 30 seconds or less, in another embodiment about 1 to 30 seconds, in another embodiment about 1 to 25 seconds, in another embodiment about 1 to 20 seconds, in another embodiment about 2 to 15 seconds. The dissolution rate is the average amount of time it takes for the film flakes to disintegrate and release observable pigment in the presence of water at room temperature, e.g. 20°-25° C. Typically, the dissolution rate can be determined in a clinical trial comprising 8 or more subjects using a toothpaste containing the film flakes and obtaining the average dissolution rate.

The film forming agent used to prepare the film matrix of the present invention is a water soluble hydroxyalkyl cellulose such as hydroxypropylmethyl cellulose, hydroxyethylpropyl cellulose, and hydroxybutylmethyl cellulose. The term "alkyl" in this context means $C_{1-4}$ alkyl. The film forming cellulose polymer is a low viscosity polymer. By low viscosity is meant a viscosity in the range of about 1 to less than about 1000 millipascal seconds (mPa·s) as determined as a 2% by weight aqueous solution of the polymer at 20° C. using a Ubbelohde tube viscometer. In a more particular embodiment the viscosity of the polymer is about 1 to about 100, more particularly about 1 to about 20, and in a particular embodiment about 1 to about 10 mPa·s at 20° C. In a preferred embodiment the hydroxyalkyl cellulose polymer is hydroxypropylmethyl cellulose polymer (HPMC).

HPMC is available commercially from the Dow Chemical Company under the trade designation Methocel E5 LV. Methocel E5 LV is a USP grade, low viscosity HPMC having 29.1% methoxyl groups and 9% hydroxyproxyl group substitution. It is a white or off-white free-flowing dry powder. As a 2 wt. % solution in water as measured with a Ubbelohde tube viscometer it has a viscosity of 5.1 mPa·s at 20° C.

The hydroxyalkyl cellulose is incorporated in the film in amounts ranging from about 10 to about 80% by weight and preferably about 30 to about 60% by weight of the film. The hydroxyalkyl cellulose polymer is incorporated into the oral composition at typically from 0.01 to 10%, more typically at from 0.05 to 5%, and most typically at from 0.1 to 1% by weight.

The film flakes typically comprises about 0.01 to 5%, more typically about 0.015 to 5%, more particularly about 0.015 to 3% of the oral composition of the invention.

The film matrix of the present invention is solubilizes in water or an aqueous solution, such as saliva, during use. During tooth brushing the mechanical action aids in rupture of the film flakes which makes the film flakes more readily soluble in the aqueous environment.

The amount of pigment in the oral composition is from 0.01 to 0.3%, more particularly from 0.02 to 0.1%, and more particularly from 0.03 to 0.08% by weight. The pigment may be uniformly spread throughout the composition or, it may be dispersed in a second phase such as a stripe or other coextruded second phase. Such "dual phase" compositions have the advantage that the phases may be differently colored, presenting a more visually attractive product to the consumer.

The pigment is violet or blue, preferably one of those listed in the Colour Index International. These pigments are listed as pigment violet 1 through to pigment violet 56 and pigment blue 1 through 83. Examples of pigment violets are pigment violet 1, 1:1, 1:2, 2, 3, 5:1, 13, 19, 23, 25, 27, 31, 32, 37, 39, 42, 44 and 50. Examples of pigment blues are pigment blue 1, 2, 9, 10, 14, 15, 15:1, 15:2, 15:3, 15:4, 15:6 16, 18, 19, 24:1, 25, 56, 60, 61, 62 and 66. Other suitable pigments are pigment ultramarine blue and ultramarine violet. The pigment should have a hue angle, h, in the CIELAB system of from 200 to 320 degrees more particularly between 250 and 290 degrees. A detailed description of hue angle may be found on p57 of Colour Chemistry 3rd edition by H. Zollinger published by Wiley-VCH. While the preferred single pigments are blue or violet, the same effect may be achieved through mixing pigments outside of this h range; for example, such a hue angle may also be obtained by mixing a red and blue pigment to yield a blue or blue-violet shaded pigment. Typically, the pigment is Pigment Blue 15, more specifically Pigment Blue 15:1, 15:2, 15:3, 15:4, 15:5 or 15:6. Typically, the pigment is capable of reflecting sufficient light such that the treated tooth is perceivably whiter than its initial color. Preferably, the pigment is colored such that its natural color is within the violet-red to green-blue color, typically from violet to blue. If a red pigment is used, the red pigment is typically present in a weight ratio of red pigment:blue pigment of about 0.1:1 to about 1:1. Examples of red pigment include Red 30, Red 40, and the like.

A pigment is generally understood to be a shade/material which is insoluble in the relevant medium, at the relevant temperature. This is in contrast to dyes which are soluble. In the context of this invention, the "relevant medium" is human saliva, the liquid medium in which the composition is used, at the temperature of the oral cavity during brushing of the teeth, i.e. up to 37° C. As a reasonable approximation, the relevant medium may be considered to be water and the relevant temperature to be 25° C.

In the context of this invention, a "soluble" hydroxyalkyl cellulose is a material that is soluble in water, typically having a solubility of 0.5% or greater, and more typically 5% or greater by weight, at 25° C. Further, such a material remains soluble following drying—i.e. it can be redissolved following drying. Such materials are are film-forming polymers. Water solubility is required in order to avoid build up of the polymer on the teeth.

The hydroxyalkyl cellulose polymer is a deposition aid, that is, it enhances deposition of the pigment onto the teeth and thereby enhances the color change caused by the pigment.

The hydroxyalkyl cellulose in the film flakes aids the deposition of the pigment onto the teeth such that tooth surface whiteness is enhanced by at least 20% and more preferably by at least 100%, in comparison to the value obtained for teeth treated in an equivalent manner with a control formulation using the same amount of pigment in the absence of the hydroxyalkyl cellulose. A method for determining tooth whiteness is described in the Examples.

Delta b* is a magnitude of color change along a yellow-blue axis, negative delta b* corresponding to reduced yellowness.

Orally Acceptable Carrier Vehicle

The oral care compositions of the invention include a vehicle or base into which the film flakes are incorporated. Examples of orally acceptable carrier vehicles include carrier polymers, humectants, water, abrasives, thickener silicas or any combination of two or more thereof. The term "orally-acceptable" refers to a polymer or ingredient which can be used to applied the to the oral cavity in a safe manner during normal use.

Carrier Polymers

Carrier polymers can comprise one or more anionic or nonionic polymers, and also may include additional polymers to adjust the viscosity of the formulation or enhance the solubility of other ingredients.

Suitable carrier polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Anionic polymers useful herein may enhance the effect of the water insoluble whitening complex, for example in an amount of from about 0.001 to about 5%, more particularly about 0.01 to 5%, more particularly about 0.05 to 4%, more particularly about 0.05 to 3% of the composition. Such agents are known generally for use in dentifrice, although not for this particular application, useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez®. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference. Another useful class of polymeric agents includes polyamino acids containing proportions of anionic surface-active amino acids such as aspartic acid, glutamic acid and phosphoserine, (in addition to the basic amino acid polymers), e.g. as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Hydroxyalkyl methyl cellulose may also be present in the non-film portion of the oral composition. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.05% to 5%, more particularly about 0.5 to 5% by weight of the total composition are used. Orally acceptable carrier polymers for use in the invention are typically water soluble. Suitable orally acceptable carrier polymers for use in the invention will generally dissolve or disperse in water at a temperature of 25° C. In addition to the hydroxyalkyl methyl cellulose in the film flakes, certain orally acceptable carrier polymers also are able to aid the deposition of the pigment onto the teeth such that tooth surface whiteness is enhanced.

The amount of orally acceptable carrier vehicle polymer in compositions of the invention, whether enhancers, deposition aids, thickeners or the like, or of a combination thereof, suitably ranges from about 0.001 to 10%, more particularly about 0.005 to 5%, more particularly about 1 to 5%, and more particularly about 1 to 3%.

Humectants

Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes about 15% to about 70% in one embodiment or about 30% to about 65% in another embodiment by weight of the dentifrice composition. Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

Abrasives

The compositions of the invention, e.g. Composition 1 et seq. may comprise a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate. The compositions may include one or more additional abrasives, for example silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof. The silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference. In certain embodiments, abrasive materials useful in the practice of the oral care compositions in accordance with the invention include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns. Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention. The abrasive is present in the oral care composition of the present invention at a concentration of about 10 to about 60% by weight, in other embodiment about 20 to about 45% by weight, and in another embodiment about 30 to about 50% by weight.

Water

Water may also be present in the oral compositions of the invention. Water, employed in the preparation of commercial oral compositions should be deionized and free of organic impurities. Water commonly makes up the balance of the compositions and includes about 0.1% to about 90%, about 10% to about 80% or about 20% to about 70%, or about 30% to about 60% by weight of the oral compositions. This amount of water includes the free water which is added plus that amount which is introduced with other materials such as with sorbitol or any components of the invention. In one embodiment no added water is included.

Product Form

Examples of suitable product forms for compositions of the invention include dentifrices, mouthwashes, chewing gums and lozenges.

A type of product form of the present invention is a dentifrice. The term "dentifrice" generally denotes formulations which are used to clean the surfaces of the oral cavity. The dentifrice is an oral composition that is not intentionally swallowed for purposes of systemic administration of therapeutic agents, but is applied to the oral cavity, used to treat the oral cavity and then expectorated. Typically the dentifrice is used in conjunction with a cleaning implement such as a toothbrush, usually by applying it to the bristles of the toothbrush and then brushing the accessible surfaces of the oral cavity. Preferably the dentifrice is in the form of a paste or a gel (or a combination thereof).

Another type of product form in the context of the present invention is a mouthwash. The term "mouthwash" generally denotes liquid formulations which are used to rinse the surfaces of the oral cavity and provide the user with a sensation of oral cleanliness and refreshment. The mouthwash is an oral composition that is not intentionally swallowed for purposes of systemic administration of therapeutic agents, but is applied to the oral cavity, used to treat the oral cavity and then expectorated. A mouthwash composition according to the invention will usually contain an aqueous continuous phase. The amount of water generally ranges from 70 to 99% by weight based on the total weight of the mouthwash.

Active Agents

The effective concentration of the active ingredients for optional use herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Active agents can include one or more of a fluoride ion source, an anti-calculus agent, an amino acid, a whitening agent, an antibacterial agent, and the like.

Arginine, where present, may be present at levels from, e.g., about 0.1 to about 20 wt % (expressed as weight of free base), e.g., about 0.1 to about 3 wt % for a mouthrinse, about 1 to about 10 wt % for a consumer toothpaste or about 7 to about 20 wt % for a professional or prescription treatment product. Fluoride where present may be present at levels of, e.g., about 25 to about 25,000 ppm, for example about 25 to about 250 ppm for a mouthrinse, about 750 to about 2,000 ppm for a consumer toothpaste, or about 2,000 to about 25,000 ppm for a professional or prescription treatment product.

Antibacterial agents may be included in the oral composition of the present invention and particularly noncationic halogenated diphenyl ethers agents which are desirable from considerations of effectiveness and safety such as 2',4,4' trichloro-2 hydroxy-diphenyl ether (Triclosan) and 2,2'-dihydroxy-5,5' dibromophenyl ether. The antibacterial agent, when present in the oral composition is present in concentrations of about 0.05 to about 2% by weight and preferably 0.1 to about 1% by weight. Levels of antibacterial agents will vary similarly, with levels used in toothpaste being e.g., about 5 to about 15 times greater than used in mouthrinse. For example, a triclosan mouthrinse may contain, e.g., about 0.03 wt % triclosan while a triclosan toothpaste may contain about 0.3 wt % triclosan.

Agents used to diminish teeth sensitivity such as potassium chloride, potassium nitrate and potassium citrate may also be included in oral compositions of the present invention at concentrations of about 0.1 to about 10% by weight.

Whitening Agents

Whitening agents which may be present in the oral composition include peroxides, metal chlorites, perborates, percarbonates, peroxyacids, persulfates, and combinations thereof. Suitable peroxide compounds include hydrogen peroxide, urea peroxide, calcium peroxide, and mixtures thereof. Suitable metal chlorites include calcium chlorite, barium chlorite, magnesium chlorite, lithium chlorite, sodium chlorite, and potassium chlorite.

Fluoride Ion Source

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counter ion in the salt.

Foaming Agents

The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox®, is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. The dosage of foaming agent in the oral care composition (i.e., a single dose) is about 0.01 to about 0.9% by weight, about 0.05 to about 0.5% by weight, and in another embodiment about 0.1 to about 0.2% by weight.

Anticalculus Agents

The oral composition can include at least one anti-calculus composition, such as one or more of the anti-calculus compositions recited in U.S. Pat. No. 5,292,526 titled "Antibacterial Anti-plaque Anticalculus Oral Composition," which is incorporated herein by reference. In various embodiments, the anti-calculus composition includes one or more polyphosphates. The anti-calculus composition can include at least one wholly or partially neutralized alkali metal or ammonium tripolyphosphate or hexametaphosphate salt present in the oral composition at an effective anti-calculus amount. The anti-calculus composition can also include at least one water soluble, linear, molecularly dehydrated polyphosphate salt effective in an anticalculus amount. The anti-calculus composition can also include a mixture of potassium and sodium salts at least one of which is present in an effective anti-calculus amount as a polyphosphate anti-calculus agent. The anti-calculus composition can also contain an effective anticalculus amount of linear molecularly dehydrated polyphosphate salt anti-calculus agent present in a mixture of sodium and potassium salts. Other useful anticalculus agents include polycarboxylate polymers and polyvinyl methyl ether/maleic anhydride (PVME/MA) copolymers, such as GANTREZ®.

Surfactants

The compositions useful in the invention may contain anionic and/or nonionic surfactants, for example:
i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate,
ii. higher alkyl sulfates, such as sodium lauryl sulfate,
iii. higher alkyl-ether sulfates, e.g., of formula $CH_3(CH_2)_m CH_2(OCH_2CH_2)_n OSO_3X$, wherein m is 6-16, e.g., 10, n is 1-6, e.g., 2, 3 or 4, and X is Na or K, for example sodium laureth-2 sulfate $(CH_3(CH_2)_{10}CH_2(OCH_2CH_2)_2OSO_3Na)$.
iv. higher alkyl aryl sulfonates such as sodium dodecyl benzene sulfonate (sodium lauryl benzene sulfonate)
v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used for a mouthwash are typically on the order of one tenth that used for a toothpaste. In one embodiment, the anionic surfactant is present in a toothpaste at from about 0.3% to about 4.5% by weight, e.g., about 1.5%.

Nonionic surfactants include nonanionic polyoxyethylene surfactants such as Polyoxamer 407, Steareth 30, Polysorbate 20, and PEG-40 castor oil and amphoteric surfactants such as cocamiopropyl betaine (tegobaine) and cocamidopropyl betaine lauryl glucoside condensation products of ethylene oxide with various hydrogen containing compounds that are reactive therewith and have long hydrophobic chains (e.g., aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides and other fatty moieties, and with propylene oxide and polypropylene oxides (e.g., Pluronic® materials).

The compositions of the invention may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the composition of the invention, e.g., Composition 1, et seq., comprises sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Flavoring Agents

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, *sassafras*, clove, sage, *eucalyptus*, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight and about 0.5 to about 1.5% by weight. The dosage of flavoring agent in the individual oral care composition dosage (i.e., a single dose) is about 0.001 to 0.05% by weight and in another embodiment about 0.005 to about 0.015% by weight.

Other Optional Ingredients

In addition to the above-described components, the embodiments of this invention can contain a variety of optional dentifrice ingredients some of which are described below. Optional ingredients include, for example, but are not limited to, adhesives, sudsing agents, sweetening agents, and additional coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material. For convenience, components of the composition of invention are expressed in the singular; however it is to be understood that mixtures of components are encompassed by use of the singular expression, for example, "an orally acceptable carrier polymer" may include mixtures of two or more polymers described herein.

The invention also includes a method for temporarily whitening teeth comprising administering an effective amount of the composition of the invention to the oral cavity of a subject in need thereof. The whitening effect of the composition is considered temporary in that it's whitening effect will noticeably diminish within about two weeks after application if not additionally treated.

The invention thus provides, in a first embodiment, an oral composition (Composition 1) comprising (i) flakes of a water soluble whitening film comprising (a) a film forming polymer comprising hydroxyalkyl cellulose, wherein the hydroxyalkyl cellulose has a viscosity of about 1 to less than about 1000 millipascal seconds (mPa·s) as determined as a 2% by weight aqueous solution of the polymer at 20° C. using a Ubbelohde tube viscometer; and (b) a pigment having a blue to violet color with a hue angle in the CIELAB system ranging from 200 to 320 degrees, wherein the dissolution rate of the film flakes is about 30 seconds or less, and (ii) an orally acceptable carrier vehicle; for example, 1.1. Composition 1 wherein the hydroxyalkyl cellulose is hydroxypropylmethyl cellulose;

1.2. Composition 1.1 wherein the pigment has a hue angle in the CIELAB system ranging from 220 to 290 degrees;

1.3. Any of the foregoing compositions wherein the pigment is blue pigment such as Pigment Blue 15;

1.4. Any of the foregoing wherein the film is free of starch;

1.5. Any of the foregoing compositions wherein the hydroxyalkyl cellulose has a viscosity of about 1 to about 100, or about 1 to about 10 millipascal seconds (mPa·s) as determined as a 2% by weight aqueous solution of the polymer at 20° C. using a Ubbelohde tube viscometer;

1.6. Any of the foregoing compositions wherein the film flakes comprise about 0.01 to 5%, more typically about 0.015 to 5%, more particularly about 0.015 to 3% of the composition of the invention;

1.7. Any of the foregoing compositions wherein the pigment comprises about 0.1 to 20%, more particularly about 1 to 10%, and more particularly about 2 to 8% of the oral composition;

1.8. Any of the foregoing compositions wherein film thickness ranges in size from about 1-4 mil, e.g., about 1.5-5 mil or about 2 mil;

1.9. Any of the foregoing compositions wherein the film flakes additionally comprise a humectant such as propylene glycol and/or a surfactant such as Polysorbate 20;

1.10. Any of the foregoing compositions wherein the particle size is such that greater than 90% of the particles pass through a 50 mesh filter, or the film flakes are 30 to 100 mesh or 30 to 80 mesh, or 50 to 100 mesh;

1.11. Any of the foregoing compositions wherein the dissolution rate is about 1 to 30 seconds, or about 1 to 25 seconds, or about 1 to 20 seconds, or about 2 to 15 seconds;

1.12. Any of the foregoing compositions wherein the orally acceptable carrier vehicle polymer is a synthetic anionic polymeric polycarboxylate;

1.13. Any of the foregoing compositions wherein the orally acceptable carrier polymer is a 1:4 to 4:1 copolymers of maleic anhydride or acid with another polymerizable ethylenically unsaturated monomer;

1.14. Any of the foregoing compositions wherein the orally acceptable carrier vehicle polymer is a methyl vinyl ether/maleic anhydride copolymer having an average molecular weight (M.W.) of about 30,000 to about 1,000,000, e.g. about 300,000 to about 800,000;

1.15. Any of the foregoing compositions wherein the orally acceptable carrier vehicle polymer is about 1-5%, e.g., about 2% of the weight of the composition;

1.16. Any of the foregoing compositions further comprising an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof;

1.17. Any of the foregoing compositions comprising L-arginine in free or orally acceptable salt form;

1.18. Any of the foregoing compositions comprising buffering agents, e.g., sodium phosphate buffer (e.g., sodium phosphate monobasic and disodium phosphate);

1.19. Any of the foregoing compositions comprising a humectant, e.g., selected from glycerin, sorbitol, propylene glycol, polyethylene glycol, xylitol, and mixtures thereof;
1.20. Any of the preceding compositions further comprising an abrasive or particulate;
1.21. The immediately preceding composition wherein the adhesive or particulate is selected from sodium bicarbonate, calcium phosphate (e.g., dicalcium phosphate dihydrate), calcium sulfate, precipitated calcium carbonate, calcium pyrophosphate, silica (e.g., hydrated silica), iron oxide, aluminum oxide, perlite, plastic particles, e.g., polyethylene, and combinations thereof,
1.22. Any of the preceding compositions comprising an abrasive in an amount of about 15 wt. % to about 70 wt. % of the total composition weight;
1.23. Any of the preceding compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from about 0.3% to about 4.5% by weight;
1.24. Any of the preceding compositions further comprising a viscosity modifying amount of one or more polymers selected from polyethylene glycols, polysaccharides (e.g., cellulose derivatives, for example carboxymethyl cellulose, polysaccharide gums, for example xanthan gum or carrageenan gum), and combinations thereof;
1.25. Any of the preceding compositions in the form of a dentifrice, mouthwash, chewing gum or lozenge;
1.26. Any of the preceding compositions further comprising flavoring, fragrance and/or coloring;
1.27. Any of the preceding compositions further comprising water:
1.28. Any of the foregoing compositions comprising one or more antibacterial agents, for example comprising an antibacterial agent selected from halogenated diphenyl ether (e.g. triclosan), herbal extracts and essential oils (e.g., rosemary extract, tea extract, *magnolia* extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride;
1.29. Any of the preceding compositions further comprising an additional whitening agent, e.g., a selected from the group consisting of peroxides, metal chlorites, perborates, percarbonates, peroxyacids, hypochlorites, and combinations thereof;
1.30. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);
1.31. Any of the preceding compositions further comprising an agent that interferes with or prevents bacterial attachment, e.g., solbrol or chitosan;
1.32. Any of the preceding compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate;
1.33. Any of the preceding compositions further comprising a soluble calcium salt, e.g., selected from calcium sulfate, calcium chloride, calcium nitrate, calcium acetate, calcium lactate, and combinations thereof;
1.34. Any of the preceding compositions further comprising a physiologically or orally acceptable potassium salt, e.g., potassium nitrate or potassium chloride, in an amount effective to reduce dentinal sensitivity;
1.35. Any of the preceding compositions further comprising a breath freshener, fragrance or flavoring;
1.36. Any of the preceding compositions effective upon application to the oral cavity, e.g., with brushing, to (i) reduce hypersensitivity of the teeth, (ii) to reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; and/or (xv) promote systemic health, including cardiovascular health, e.g., by reducing potential for systemic infection via the oral tissues;
1.37. A composition obtained or obtainable by combining the ingredients as set forth in any of the preceding compositions;
1.38. Any of the preceding compositions which does not contain Gantrez® (copolymers of maleic anhydride and with methyl vinylether);
1.39. Any of the preceding compositions further comprising effective amounts of additional agents selected from fluoride, I-arginine in free or orally acceptable salt form, antibacterial agents in addition to the gallium salt and the basic amino acid polymer, anti-inflammatory compounds, and whitening agents;
1.40. Any of the preceding compositions wherein the composition is a toothpaste or mouthwash optionally further comprising one or more of one or more of water, abrasives, surfactants, foaming agents, vitamins, polymers, enzymes, humectants, thickeners, antimicrobial agents, preservatives, flavorings, colorings and/or combinations thereof;

1.41. Any of the preceding compositions wherein the composition is toothpaste.

All references cited herein are hereby incorporated by referenced in their entireties. In the event of a conflict in a definition in the present disclosure and that of a cited reference, the present disclosure controls.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight.

EXAMPLES

Example 1

Simple solutions were prepared in water and consisted of 2% of a polymeric deposition aid and 0.05% of blue pigment 15. The pH of each solution was adjusted to pH 7 to model the pH of the mouth during product use.

The polymeric deposition aids tested were hydroxypropylmethylcellulose (HPMC-Methocel E5), polyvinylpyrrolidone (PVP K-90), and Gantrez S-97.

Experimental Method for Evaluating Retention of Blue Pigment on Teeth from Solution:

The roots of human third molars were removed and the tooth was bisected from the crown through the root. Each half of the tooth was mounted, enamel side facing out, in a tray using a thermal impression compound. Surface stains were removed from the teeth through brushing with a control silica toothpaste (10 min brushing with a 1:2 (w/w) slurry, 120 strokes/min). The teeth were again rinsed with deionized water and cool air was used to remove excess water. The color values were measured with the spectrophotometer (Spectroshade Micro, MHT technologies). The teeth were next soaked in saliva for 15 min and then the saliva was removed. For the measurement of the blue retention, 10 g of simple solution was weighed into the tray. The teeth were soaked for 2 min. The solution was then rinsed with 100 mL of deionized water and cool air was used to remove excess water. Finally, the color values were measured with the spectrophotometer. $\Delta b^*$ is the change from yellow to blue with a negative value indicating a shift to blue. This is the metric by which the deposition of blue pigment can be quantified. The $\Delta b^*$ reported is the difference between the $b^*$ values of the tooth after surface stains are removed to that after soaking with the product containing blue pigment.

TABLE 1

| Simple solution composition | Molecular Weight | $\Delta b^*$ |
| --- | --- | --- |
| Gantrez S-97 | 1,500,000 | −0.8 ± 0.8 |
| PVP K-90 | 1,300,000 | −0.4 ± 0.4 |
| HPMC, Methocel E5 | 18,000-22,000 | −0.5 ± 0.2 |

The data in table 1 indicates that there is not a correlation between high molecular weight and increased deposition of blue pigment by a polymer as EP1935395A1 claims. Other factors such as chemical functionality and water solubility may also play a significant role in the ability of a polymer to deposit a hydrophobic substance on teeth. High molecular weight PVP is no better than HPMC at delivering blue pigment to teeth despite having a greater molecular weight.

Example 2

Dentifrice Formula Preparation

Films were cast containing blue pigment, specifically blue pigment 15. The only film forming material in the formula is a HPMC polymer, specifically sold under the trade name Methocel E5 from Dow Corning. Methocel E5 is a low molecular weight HPMC having a viscosity of a 2% solution at 20° C. and 10 s-1 of 4-6 mPa·s.

TABLE 2

| Description | Perfect Time film comp. |
| --- | --- |
| HPMC E5 | 55.20 |
| Blue 15 | 16.90 |
| Red 30 | 3.40 |
| Propylene Glycol | 20.70 |
| Tween 80 | 3.80 |

The films were cut into squares or ground into small speckles after casting. These small films were incorporated into a dentifrice formula having the general composition listed in Table 3 column A.

TABLE 3

| Ingredient | (A) wt % | (B) wt % | (C) wt % |
| --- | --- | --- | --- |
| Sorbitol | Q.S. | Q.S. | Q.S. |
| Silica | 22.00 | 22.00 | 22.00 |
| Water | 20.00 | 20.00 | 20.00 |
| Glycerin | 10.00 | 10.00 | 10.00 |
| Thickening Silica | 4.00 | 4.00 | 4.00 |
| Polyethylene glycol | 3.00 | 3.00 | 3.00 |
| Sodium tripolyphosphate | 3.00 | 3.00 | 3.00 |
| Tetrapotassium pyrophosphate | 2.44 | 2.44 | 2.44 |
| Sodium lauryl sulfate | 1.50 | 1.50 | 1.50 |
| Flavor | 1.50 | 1.50 | 1.50 |
| Cocamidopropylbetaine | 1.25 | 1.25 | 1.25 |
| Sodium carboxymethylcellulose | 0.50 | 0.50 | 0.50 |
| Sodium fluoride | 0.32 | 0.32 | 0.32 |
| Sodium saccharin | 0.30 | 0.30 | 0.30 |
| Film containing pigment blue 15 | 0.30 | 0.00 | 0.00 |
| Sodium hydroxide | 0.27 | 0.27 | 0.27 |
| mica | 0.10 | 0.10 | 0.10 |
| Pigment blue 15 | 0.00 | 0.075 | 0.05 |
| HPMC E5 (Methocel) | 0.00 | 0.00 | 0.17 |
| Pigment Red 30 | 0.00 | 0.00 | 0.01 |
| Propylene Glycol | 0.00 | 0.00 | 0.06 |
| Tween 80 | 0.00 | 0.00 | 0.01 |

Experimental Method for Evaluating Retention of Blue Pigment on Teeth from Dentifrice:

The roots of human third molars were removed and the tooth was bisected from the crown through the root. Each half of the tooth was mounted, enamel side facing out, in a tray using a thermal impression compound. Surface stains were removed from the teeth either through brushing with a control silica toothpaste (2 min brushing with a 1:2 (w/w) slurry, 120 strokes/min) or by using a dental prophylaxis (5 sec application). The teeth were rinsed with deionized water and cool air was used to remove excess water. The color values were measured with the spectrophotometer (Spectroshade Micro, MHT technologies). For the measurement of the blue retention, 6 g of the sample toothpaste was weighed into the tray. 12 mL of deionized water or saliva was added to the tray. The teeth were brushed for 2 min at 120 strokes per min and with 250 grams of applied force on a brushing machine. The toothpaste was then rinsed with 100 mL of deionized water and cool air was used to remove excess water. Finally, the color values were measured with the spectrophotometer. Δb* is the change from yellow to blue with a negative value indicating a shift to blue. This is the metric by which the deposition of blue pigment can be quantified. The Δb* reported is the difference between the b* values of the tooth after surface stains are removed to that after brushing with the product containing blue pigment. A change in a whiteness index (WIO) can also be reported to show that the deposition of blue pigment results in an increase in the whiteness of a tooth.

TABLE 4

| Formula Composition | Δb* |
|---|---|
| (B) 0.075% blue pigment | −0.2 ± 0.3 |
| (A) 0.050% blue pigment (0.3% 0.040 sq in HPMC square film) | −1.3 ± 1.8 |

The results in Table 5 demonstrate that the delivery of blue pigment from a dentifrice containing blue pigment in a film composed of HPMC polymer is greater than the delivery of blue pigment from dentifrice without the film.

TABLE 5

| Formula composition | Δb* | ΔWIO |
|---|---|---|
| Clinically tested commercial product having blue pigment and Gantrez polymer (Signal White Now) | −1.4 ± 0.5 | 3.2 ± 1.5 |
| (A) 0.050% blue pigment (0.3% HPMC film, 30-50 mesh ground films) | −1.2 ± 0.6 | 4.7 ± 2.1 |
| (A)0.050% blue pigment (0.3% HPMC film, 50 mesh ground films) | −1.4 ± 0.6 | 5.2 ± 1.4 |
| (C)0.050% blue pigment (film ingredients added to formula individually) | −0.9 ± 0.6 | 2.8 ± 2.1 |

The results in Table 5 show that the delivery of blue pigment from different sizes of HPMC films is on par with the delivery of blue pigment from a formula containing gantrez polymer. Furthermore, the delivery of blue pigment resulted in an increase in whiteness as shown in the positive change in the WIO whitening index. The formula containing blue pigment and gantrez polymer is sold under the name Signal White Now and it has been clinically documented to deliver blue pigment in-vivo for a measurable increase in the whiteness of teeth (Joiner, 2008). The results in table 5 also indicate that HPMC polymer is capable of delivering blue pigment to teeth when incorporated into a dentifrice formula. However, the ability of HPMC to deliver blue pigment appears to enhanced when the HPMC is premixed and concentrated with the blue pigment in a film strip. The blue pigment and HPMC remain together in the film until the time of brushing when the film strip dissolves. In table 5 the formula A options having HPMC blue pigment films (50-mesh) provide statistically superior whitening to formula C. The statistical comparison was made using the student T-Test in which a p<0.05 indicates a statistically significant different between products.

Example 3

Dissolution Rate

The dissolution rate of toothpastes comprising film flakes of the invention containing blue pigment and having a film thickness of 2 mil and a particle size such that greater than 90% of the particles pass through a 50 mesh filter are tested in an in-vivo trial. As can be seen in Table 6, the average dissolution time for the first appearance of color was 13.6 seconds.

TABLE 6

| Panelist | Time to first notice of blue color in film (sec) | Time to Max color (sec) |
|---|---|---|
| 1 | 9 | 75 |
| 2 | 10 | 55 |
| 3 | 15 | 60 |
| 4 | 13 | 45 |
| 5 | 8 | 12 |
| 6 | 20 | 40 |
| 7 | 15 | 30 |
| 8 | 25 | 50 |
| 9 | 19 | 49 |
| 10 | 2 | 60 |
| Average | 13.6 | 47.6 |

What is claimed is:

1. A tooth whitening oral care composition comprising:
   (i) film flakes of a single-layer water-soluble whitening film comprising
      (a) a film forming polymer comprising hydroxyalkyl cellulose wherein the hydroxyalkyl cellulose has a viscosity of about 1 to less than about 1000 millipascal seconds (mPa·s) as determined as a 2% by weight aqueous solution of the polymer at 20° C. using a Ubbelohde tube viscometer; and
      (b) a pigment having a blue to blue-violet color with a hue angle in the CIELAB system ranging from 220 to 320 degrees, wherein the film flakes have a dissolution rate of about 30 seconds or less, and
   (ii) an orally acceptable carrier vehicle;
   wherein the particle size of the film flakes is 30 to 80 mesh.

2. The composition of claim 1, wherein the hydroxyalkyl cellulose is hydroxypropylmethyl cellulose.

3. The composition of claim 1 wherein the particle size of the film flakes is 50 to 80 mesh.

4. The composition of claim 1 wherein the dissolution rate is about 1 to 30 seconds.

5. The composition of claim 1 wherein the film flakes comprise about 0.01 to 5% of the composition.

6. The composition of claim 1 wherein the hydroxyalkyl cellulose has a viscosity of about 1 to about 10 millipascal seconds (mPa·s) as determined as a 2% by weight aqueous solution of the polymer at 20° C. using a Ubbelohde tube viscometer.

7. The composition of claim 1, wherein film is free of starch.

8. The composition of claim 1, wherein the pigment is Pigment Blue #15.

9. The composition of claim 1, wherein the film flakes additionally comprise a humectant and/or a surfactant.

10. The composition of claim 1, wherein the orally acceptable vehicle carrier comprises about 1-5% of the weight of the composition.

11. The composition according to claim 1, further comprising an effective amount of an additional agent selected from fluoride, arginine in free or orally acceptable salt form, an antibacterial agent, an anti-inflammatory agent, a whitening agent, and a combination of two or more thereof.

12. The composition of claim 1 in the form of a dentifrice, mouthwash, chewing gum or lozenge.

13. The composition according to claim 1 wherein the composition is a toothpaste comprising one or more of an water, an abrasive, a surfactant, a foaming agent, a vitamin, a polymer, an enzyme, a humectant, a thickener, an antimicrobial agent, a preservative, a flavoring, a coloring and/or a combination of two or more thereof.

14. A method for temporarily whitening teeth comprising administering an effective amount of a composition according to claim 1 to the oral cavity of a subject in need thereof.

15. The composition of claim 2, wherein the hydroxypropylmethyl cellulose is premixed and concentrated with the pigment in a film strip.

16. The composition of claim 1, wherein the film flakes comprise about 0.105 to 5% of the composition.

17. The composition of claim 1, wherein the film flakes comprise about 0.105 to 3% of the composition.

18. A tooth whitening oral care composition comprising:
 (i) film flakes of a single-layer water-soluble whitening film comprising
  (a) a film forming polymer consisting essentially of hydroxyalkyl cellulose wherein the hydroxyalkyl cellulose has a viscosity of about 1 to less than about 1000 millipascal seconds (mPa·s) as determined as a 2% by weight aqueous solution of the polymer at 20° C. using a Ubbelohde tube viscometer; and
  (b) a pigment having a blue to blue-violet color with a hue angle in the CIELAB system ranging from 220 to 320 degrees,
   wherein the film flakes have a dissolution rate of about 30 seconds or less, and
 (ii) an orally acceptable carrier vehicle;
 wherein the particle size of the film flakes is 30 to 80 mesh.

19. The composition of claim 18, wherein the hydroxyalkyl cellulose is hydroxypropylmethyl cellulose.

* * * * *